US00PP26997P2

(12) United States Plant Patent
van Nijnatten

(10) Patent No.: US PP26,997 P2
(45) Date of Patent: Aug. 2, 2016

(54) *ILEX* PLANT NAMED 'ANNYS1'

(50) Latin Name: *Ilex crenata*
Varietal Denomination: Annys1

(71) Applicant: Andre Franciscus van Nijnatten, Zundert (NL)

(72) Inventor: Andre Franciscus van Nijnatten, Zundert (NL)

( * ) Notice: Subject to any disclaimer, the term of this patent is extended or adjusted under 35 U.S.C. 154(b) by 63 days.

(21) Appl. No.: 14/121,959

(22) Filed: Nov. 7, 2014

(51) Int. Cl.
*A01H 5/00* (2006.01)

(52) U.S. Cl.
USPC ..... Plt./247

(58) Field of Classification Search
USPC ..... Plt./247
See application file for complete search history.

(56) References Cited

PUBLICATIONS

PLUTO Plant Variety Database Mar. 5, 2016. p. 1.*

* cited by examiner

*Primary Examiner* — Annette Para
(74) *Attorney, Agent, or Firm* — C. A. Whealy

(57) ABSTRACT

A new and distinct *Ilex* plant named 'Annys1', characterized by its compact and rounded plant habit; freely branching habit; dense and bushy growth habit; leaves that are initially green in color and with development, become golden yellow in color; leaves that resist sun-burning; and good garden performance and winter hardiness.

2 Drawing Sheets

Botanical designation: *Ilex crenata.*
Cultivar denomination: 'ANNYS1'.

BACKGROUND OF THE INVENTION

The present Invention relates to a new and distinct *Ilex* plant, botanically known as *Ilex crenata* and hereinafter referred to by the name 'Annys1'.

The new *Ilex* plant is a product of a planned breeding program conducted by the Inventor in Zundert, The Netherlands. The objective of the breeding program is to create new compact *Ilex* plants with golden yellow-colored leaves and winter hardiness.

The new *Ilex* plant originated from a cross-pollination made by the Inventor in 2001 of two unnamed proprietary selections of *Ilex crenata*. The new *Ilex* plant was discovered and selected by the Inventor as a single plant from within the progeny of the stated cross-pollination in a controlled environment in Zundert, The Netherlands in 2008.

Asexual reproduction of the new *Ilex* plant by cuttings in a controlled greenhouse environment in Zundert, The Netherlands since 2010 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Annys1' and in combination distinguish 'Annys1' as a new and distinct *Ilex* plant:

1. Compact and rounded plant habit.
2. Freely branching habit; dense and bushy growth habit.
3. Leaves that are initially green in color and with development, become golden yellow in color.
4. Leaves that resist sun-burning.
5. Good garden performance and winter hardiness.

Plants of the new *Ilex* differ from plants of the parent selections primarily in plant habit and leaf coloration.

Plants of the new *Ilex* can be compared to the plants of *Ilex crenata* 'Convexed Gold', not patented. In side-by-side comparisons plants of the new *Ilex* differed from plants of 'Convexed Gold' in the following characteristics:

1. Plants of the new *Ilex* were more compact than plants of 'Convexed Gold'.
2. Plants of the new *Ilex* were more mounding than and not as upright as plants of 'Convexed Gold'.
3. Leaves of plants of the new *Ilex* were more cupped than and not as flat as leaves of plants of 'Convexed Gold'.

BRIEF DESCRIPTION OF THE PHOTOGRAPHS

The accompanying colored photographs illustrate the overall appearance of the new *Ilex* plant showing the colors as true as it is reasonably possible to obtain in colored reproductions of this type. Colors in the photographs may differ slightly from the color values cited in the detailed botanical description, which accurately describe the colors of the new *Ilex* plant.

The photograph on the first sheet is a side perspective view of a typical immature plant of 'Annys1' grown in a container.

The photograph on the second sheet is a close-up view of a typical mature plant of 'Annys1' showing the golden yellow leaf coloration.

DETAILED BOTANICAL DESCRIPTION

Plants used in the aforementioned photographs and following observations and measurements were grown in one-gallon containers in a polyethylene-covered greenhouse in Grand Haven, Mich. and under cultural practices typical of commercial *Ilex* production. Plants were two and three years old when the photographs and detailed description were taken. In the following description, color references are made to The Royal Horticultural Society Colour Chart, 1995 Edition, except where general terms of ordinary dictionary significance are used.

Botanical classification: *Ilex crenata* 'Annys1'.

Parentage:

*Female, or seed, parent*.—Unnamed proprietary selection of *Ilex crenata*, not patented.

*Male, or pollen, parent*.—Unnamed proprietary selection of *Ilex crenata*, not patented.

Propagation:

*Type*.—By cuttings.

*Time to produce a rooted young plant, summer*.—About four weeks at temperatures about 16° C. to 18° C.

*Time to produce a rooted young plant, winter*.—About five months at air temperatures about 8° C.

*Root description*.—Medium in thickness, fibrous; brown in color.

*Rooting habit*.—Freely branching; dense.

Plant description:

*Plant and growth habit*.—Perennial shrub; compact and rounded plant habit; vigorous growth habit.

*Branching habit*.—Freely branching habit; dense and bushy growh habit with about twelve primary lateral branches developing per plant.

*Plant height*.—About 21 cm.

*Plant diameter, area of spread*.—About 33 cm.

*Lateral branch description*.—Length: About 18 cm to 21 cm. Diameter: About 3 mm. Internode length: About 5 mm. Strength: Strong. Texture: Smooth, glabrous. Color, developing: Close to 145A. Color, fully developed: Close to 137C.

Leaf description:

*Arrangement*.—Alternate, simple.

*Length*.—About 2 cm.

*Width*.—About 1 cm.

*Shape*.—Elliptic.

*Apex*.—Obtuse.

*Base*.—Obtuse, rounded.

*Margin*.—Entire to slightly serrate.

*Venation pattern*.—Pinnate.

*Texture, upper and lower surfaces*.—Smooth, glabrous.

*Color*.—Developing leaves, upper surface: Close to 154A. Developing leaves, lower surface: Close to 151C. Fully expanded leaves, upper surface: Close to 135A; venation, close to 150B; color of fully matured plants, close to 13C and venation, close to 13C. Fully expanded leaves, lower surface: Close to 137C; venation, close to 145A.

*Petioles*.—Length: About 4 mm. Diameter: About 2 mm. Texture, upper and lower surfaces: Smooth, glabrous. Color, upper and lower surfaces of upper leaves: Close to 145B. Color, upper and lower surfaces of lower (shaded) leaves: Close to 144A.

Flower description:

*Flower appearance and arrangement*.—Single axillary rotate flowers; flowers face upright to outwardly.

*Natural flowering season*.—Plants flower in the early spring in Michigan; flowers not persistent.

*Fragrance*.—None detected.

*Flower diameter*.—About 3 mm.

*Flower length (height)*.—About 7 mm.

*Flower buds*.—Length: About 3 mm. Diameter: About 2 mm. Shape: Obovate. Color: Close to 155A.

*Petals*.—Quantity and arrangement: About four in a single whorl. Length: About 3 mm. Width: About 2 mm. Shape: Oblong to obovate. Apex: Obtuse. Base: Obtuse. Margin: Entire. Texture, upper and lower surfaces: Smooth, glabrous. Color: When opening, upper and lower surfaces: Close to 155A. Fully opened, upper and lower surfaces: Close to 155A; color does not change with development.

*Sepals*.—Quantity and arrangement: About four in a single whorl. Length: Less than 1 mm. Diameter: Less than 1 mm. Shape: Obovate. Apex: Acute. Base: Truncate. Margin: Entire. Texture, upper and lower surfaces: Smooth, glabrous. Color, upper and lower surfaces: Close to 145A.

*Peduncles*.—Length: About 5 mm. Diameter: About 1 mm. Strength: Strong. Aspect: Upright to outwardly. Texture: Smooth, glabrous. Color: Close to 145A.

*Reproductive organs*.—Androecium: Quantity per flower: About four. Filament length: About 1 mm. Filament color: Close to 155D. Anther length: About 0.5 mm. Anther shape: Round. Anther color: Close to 155D. Pollen amount: Scarce. Pollen color: Close to 155D. Gynoecium: Quantity per flower: One. Pistil length: About 1 mm. Style length: About 0.5 mm. Style color: Close to 144A. Stigma shape: Rounded. Stigma color: Close to 144B. Ovary color: Close to 144A.

*Seeds and fruits*.—Seed and fruit development have not been observed on plants of the new *Ilex*.

Garden performance: Plants of the new *Ilex* have been observed to have good garden performance and to be tolerant to rain, wind and suitable for USDA Hardiness Zones 5 to 8. Leaves of plants of the new *Ilex* resist sun-burning.

Pathogen & pest resistance: Plants have not been observed to be resistant to pathogens and pests common to *Ilex* plants.

It is claimed:

1. A new and distinct *Ilex* plant named 'Annys1' as illustrated and described.

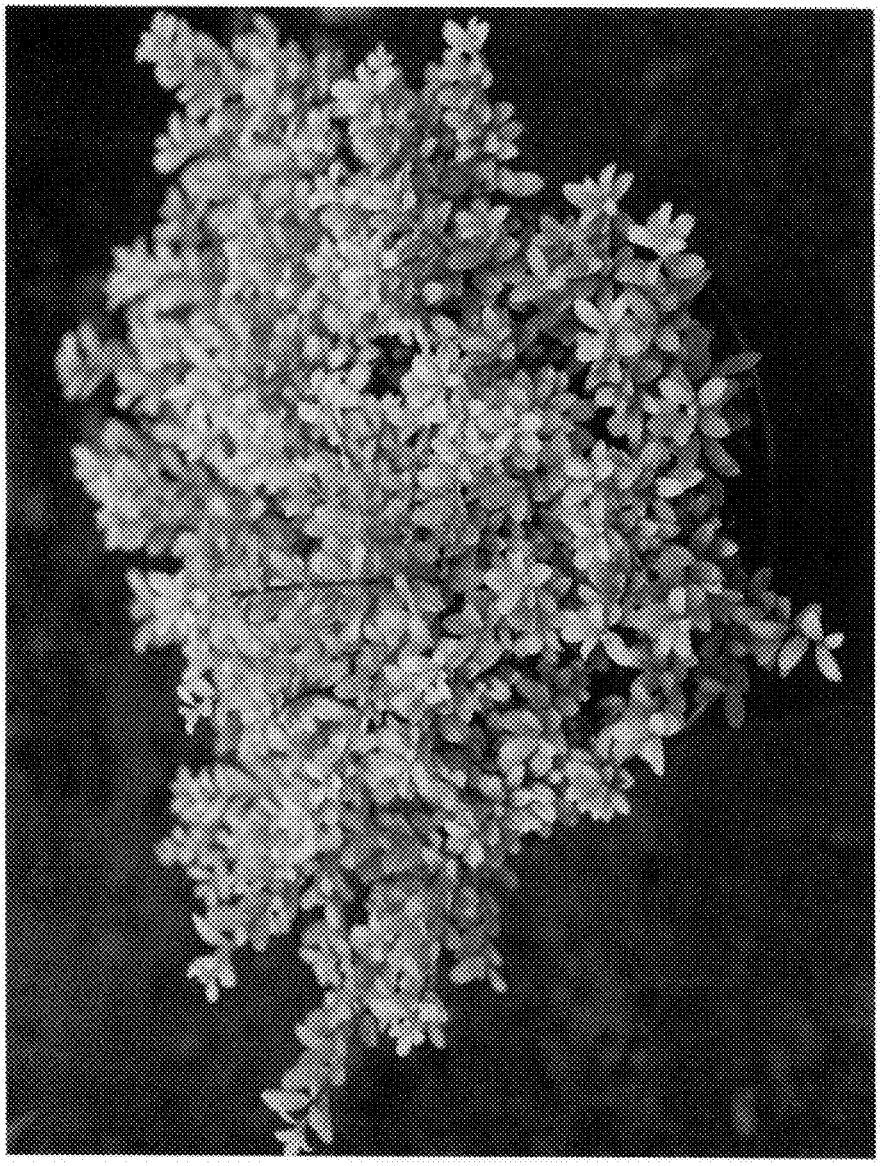

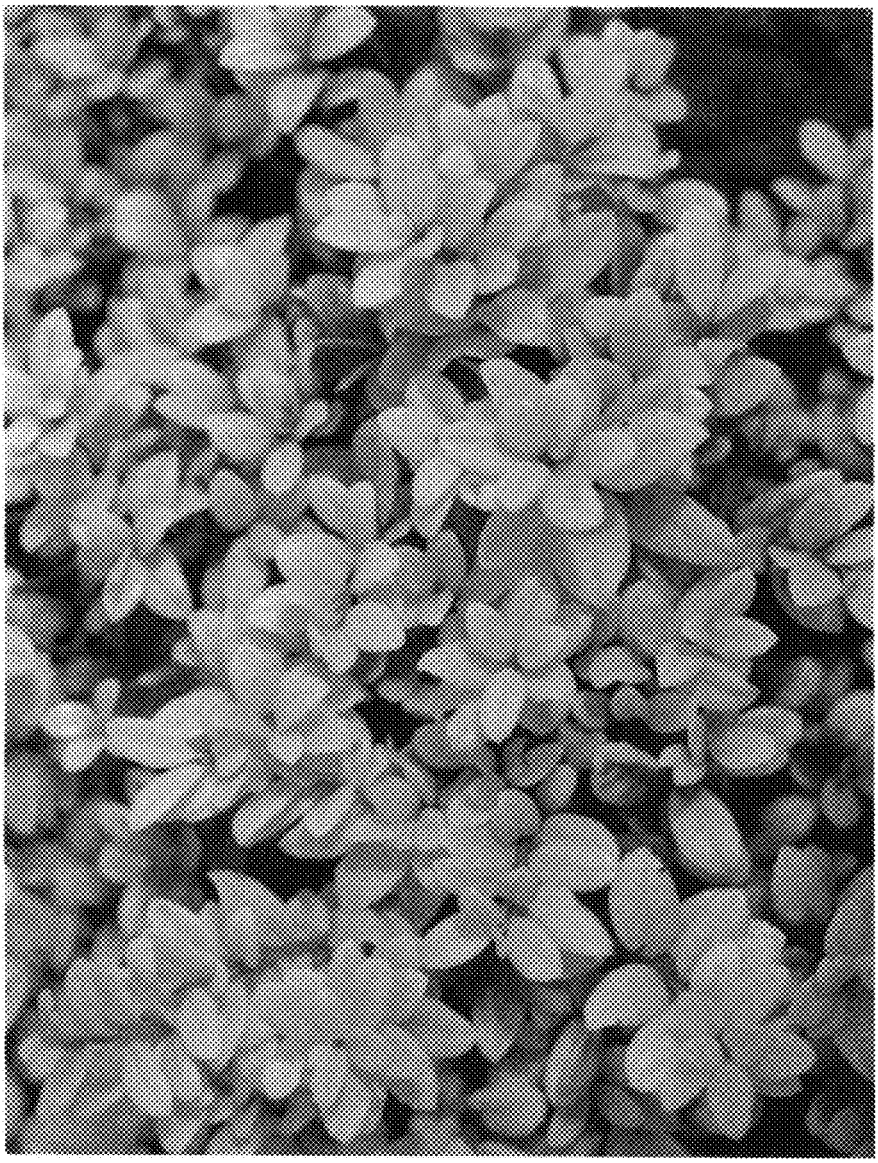

* * * * *